US007858772B2

(12) United States Patent
Gupta et al.

(10) Patent No.: US 7,858,772 B2
(45) Date of Patent: Dec. 28, 2010

(54) COMPOUNDS AND METHODS FOR SYNTHESIS AND PURIFICATION OF OLIGONUCLEOTIDES

(75) Inventors: Amar Gupta, Danville, CA (US); Stephen Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 381 days.

(21) Appl. No.: 11/959,443

(22) Filed: Dec. 18, 2007

(65) Prior Publication Data
US 2008/0161548 A1 Jul. 3, 2008

Related U.S. Application Data

(60) Provisional application No. 60/871,733, filed on Dec. 22, 2006.

(51) Int. Cl.
C07H 21/00 (2006.01)
(52) U.S. Cl. ............... 536/25.34; 536/25.3; 536/25.31; 536/25.32; 536/25.33
(58) Field of Classification Search .................. None
See application file for complete search history.

(56) References Cited

U.S. PATENT DOCUMENTS

| 4,469,863 | A | 9/1984 | Ts'o et al. |
|---|---|---|---|
| 4,816,571 | A | 3/1989 | Andrus et al. |
| 5,034,506 | A | 7/1991 | Summerton et al. |
| 5,216,141 | A | 6/1993 | Benner |
| 5,235,033 | A | 8/1993 | Summerton et al. |
| 5,386,023 | A | 1/1995 | Sanghvi et al. |
| 5,602,240 | A | 2/1997 | De Mesmaeker et al. |
| 5,637,684 | A | 6/1997 | Cook et al. |
| 5,644,048 | A | 7/1997 | Yau |
| 5,990,303 | A | 11/1999 | Seela |
| 6,107,479 | A | 8/2000 | Natt et al. |
| 7,135,565 | B2 | 11/2006 | Dellinger et al. |
| 7,271,258 | B2 | 9/2007 | Dollinger et al. |
| 2002/0055623 | A1 | 5/2002 | Cheruvallath et al. |
| 2006/0178507 | A1 | 8/2006 | Berry et al. |

FOREIGN PATENT DOCUMENTS

| EP | 2007011315 | 5/2008 |
|---|---|---|
| WO | WO 03/062452 A2 | 7/2003 |
| WO | 2006081035 A2 | 8/2006 |
| WO | 2006081035 A3 | 8/2006 |
| WO | WO 2006/081035 | 8/2006 |

OTHER PUBLICATIONS

Pearson, W. H., et al., 2005, "Fluorous Affinity Purification of Oligonucleotides", *J. Org. Chem.*, 70:7114-7122.
Beller, "Noncovalent attachment of nucleotides by fluorous—fluorous interactions: application to a simply purification principle for synthetic DNA fragments." *Helv. Chim. Acta.*, 88: 171-179, 2005.
Brittain et al., "Enrichment and analysis of peptide subsets using fluorous affinity tags and mass spectrometry." *Nature Biotechnol.*, 23(4): 463-468, 2005.
de Visser et al., "A novel, base-labile fluorous amine protecting group, synthesis and use as a tag in the purification of synthetic peptides." *Tetrahedron Letters*, 44:9013-9016, 2003.
Filippov et al., "Use of benzyloxycarbonyl (Z)-based fluorophilic tagging reagents in the purification of synthetic peptides." *Tetrahedron Letters*, 43: 7809-7812, 2002.
Goto et al., "Rapid oligosaccharide synthesis on a novel benzyl-type fluorous support." *Synlett*, 2003, No. 12, pp. 2221-2223.
Manzoni, "Rapid synthesis of oligosaccharides using an anomeric fluorous silyl protecting group." *Chem. Commun.*, 2003, pp. 2930-2931.
Markowicz et al., "Fluorous coupling reagents: application of 2-chloro-4,6-bis[(heptadecafluorononyl)oxy]-1,3,5-triazine in peptide synthesis." *Synthesis*, 2004, No. 1, pp. 80-86.
Mizuno et al., "Fluorous glycopeptide synthesis without protection of sugar hydroxyl groups." *Chem. Letters*, 34(3): 426-427, 2005.
Montanari et al., "Just add water: a new fluorous capping reagent for facile purification of peptides synthesized on the solid phase." *J. Am. Chem. Soc.*, 126: 9528-29, 2004.
Palmacci et al., "'Cap Tag'—Novel methods for the rapid purification of oligosaccharides prepared by automated solid-phase synthesis." *Angew. Chem. Int. Ed.*, 40(23): 4433-4437, 2001.
Hadimani, Mallinath B., et al., 2003, "Synthesis, In Vitro, and In Vivo Evaluation of Phosphate Ester Derivatives of Combretastatin A-4", Bioorganic & Medicinal Chemistry Letters, 13:1505-1508.

*Primary Examiner*—Patrick T Lewis
(74) *Attorney, Agent, or Firm*—Townsend and Townsend and Crew LLP

(57) ABSTRACT

The present invention provides methods of extending nucleic acids and purifying target nucleic acids. The methods include the use of capping reagents to effect chain termination and provide a handle for purification via fluorous affinity methods.

17 Claims, 4 Drawing Sheets

Fig. 1 - Solid-Phase Oligonucleotide Synthesis Cycle
1. 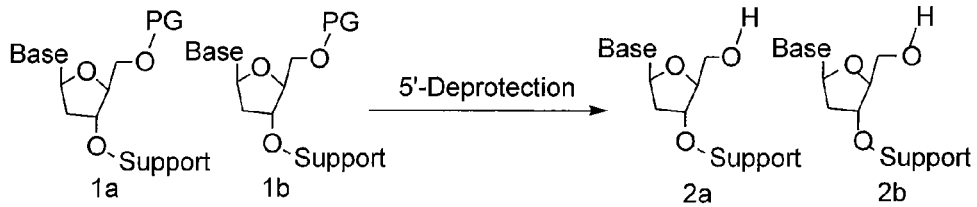
2. 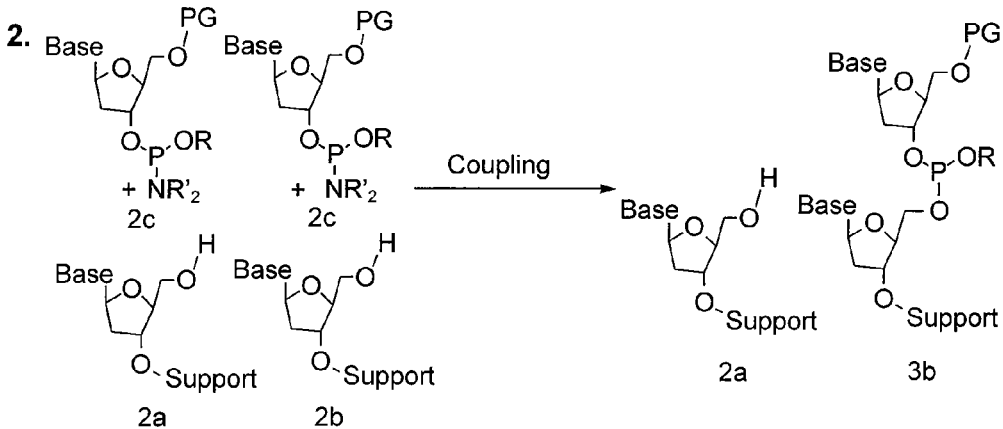
3. 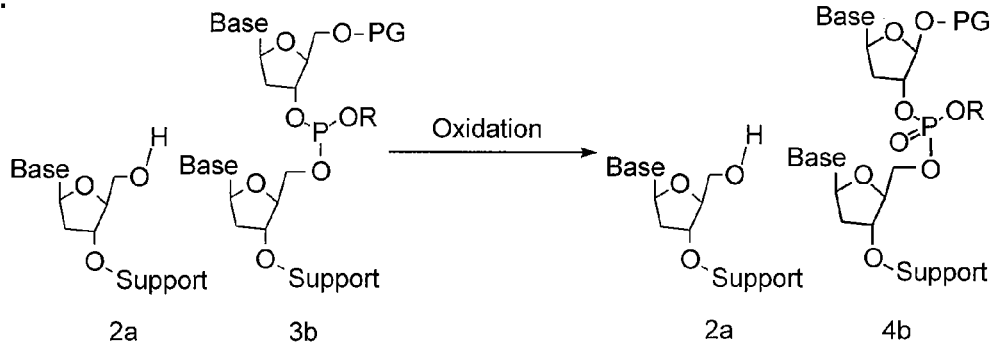
4. 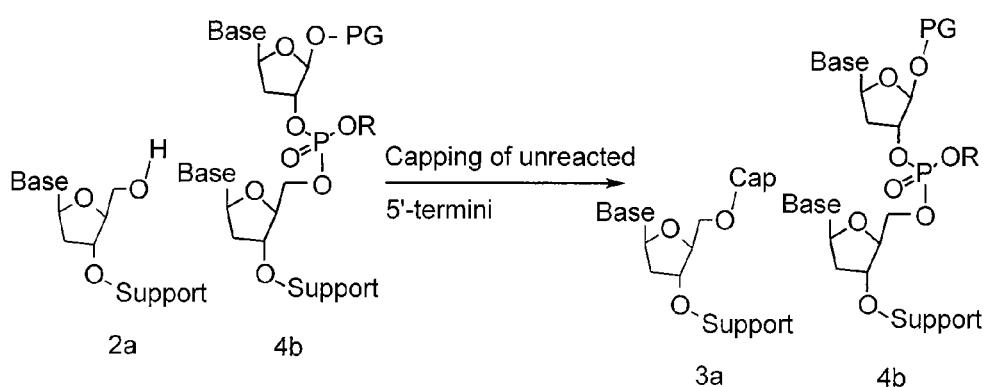

Fig. 2 - Cleavage from the solid support
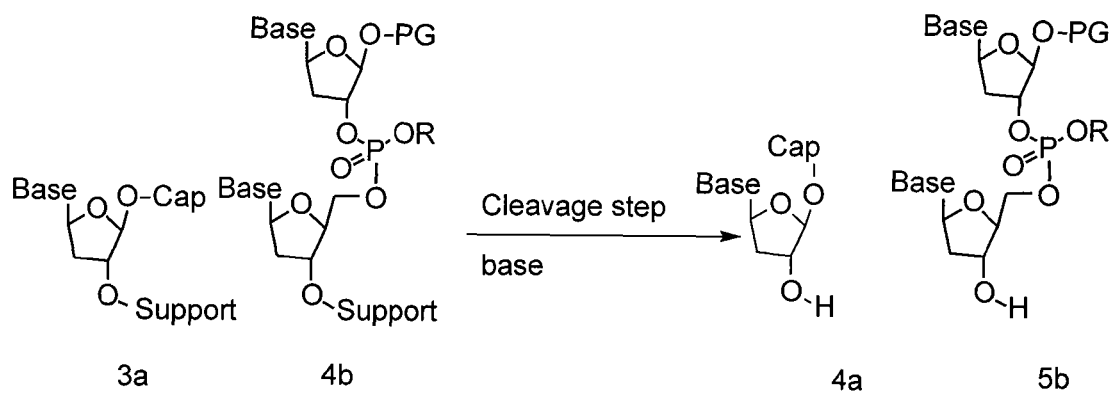
Fig. 3 - Synthesis of fluorous phosphoramidite capping reagent
a.
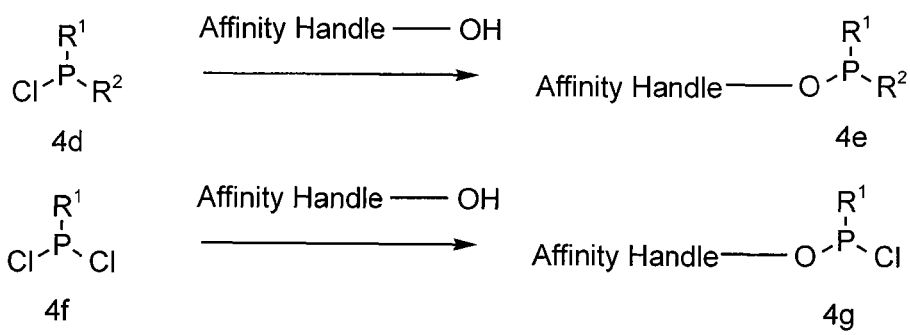
b.
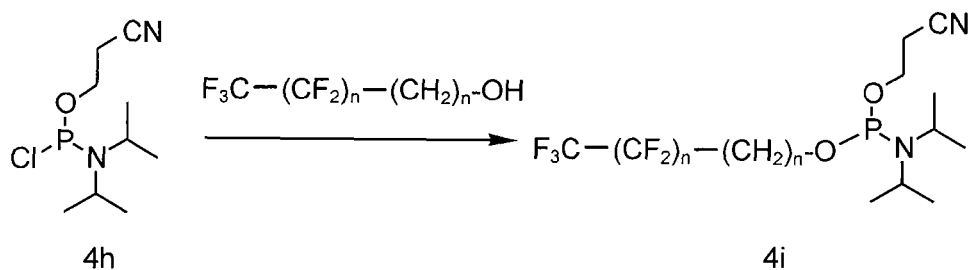

Fig. 4 - Fluorous-affinity purification
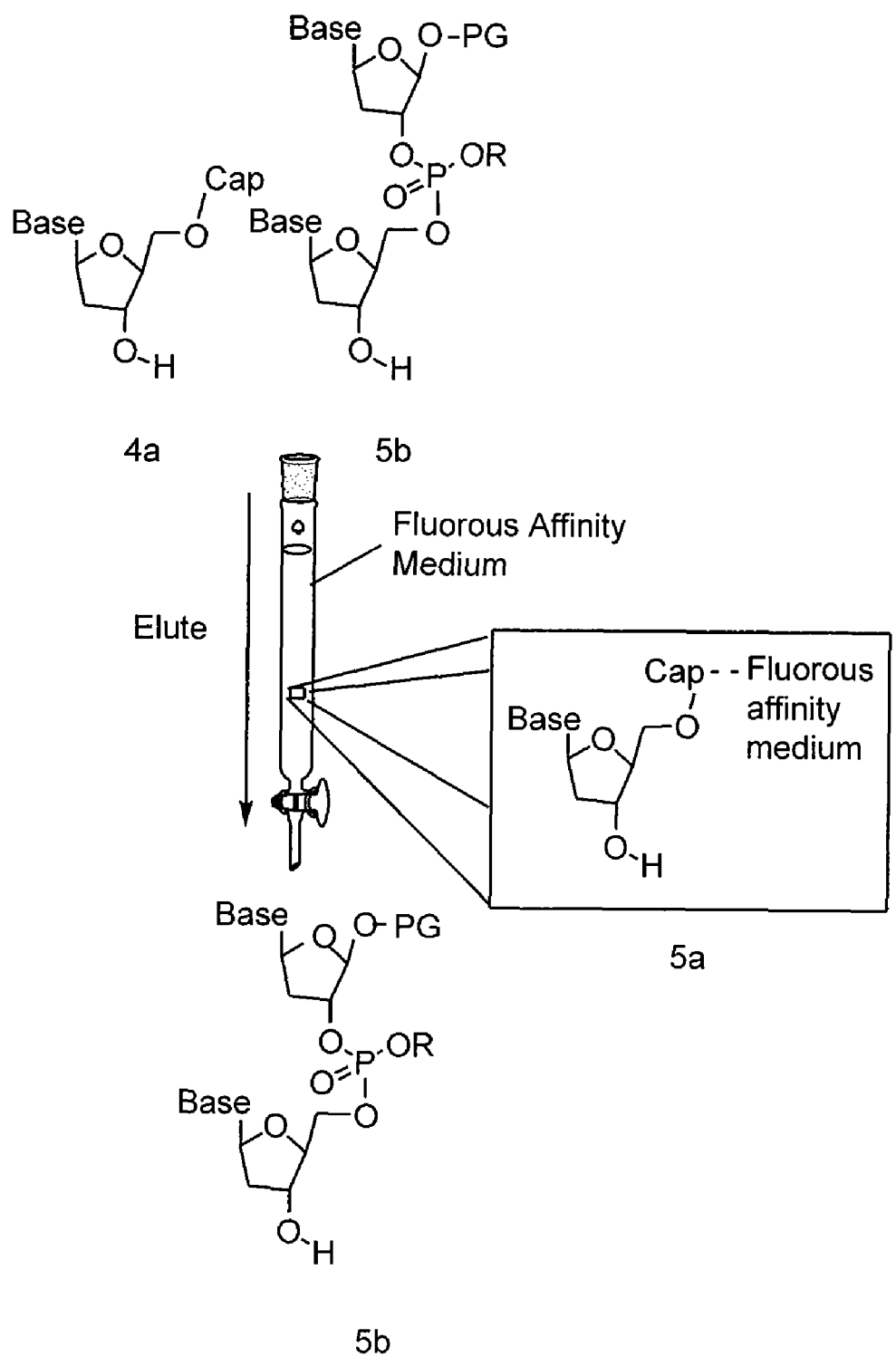

Fig. 5 - HPLC analysis of crude product
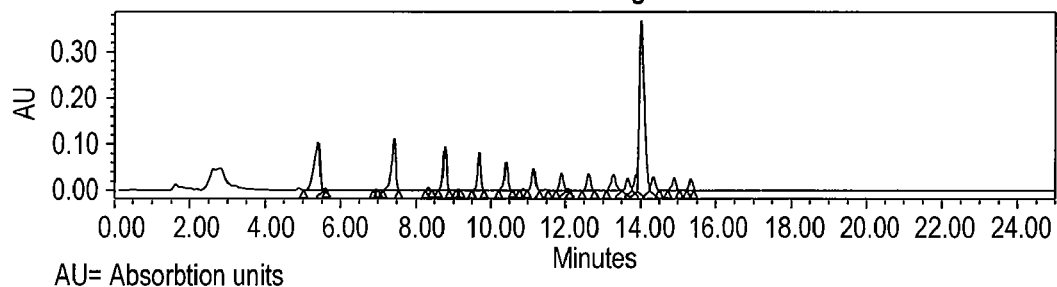
AU= Absorbtion units
Fig. 6 - HPLC analysis of filtrate
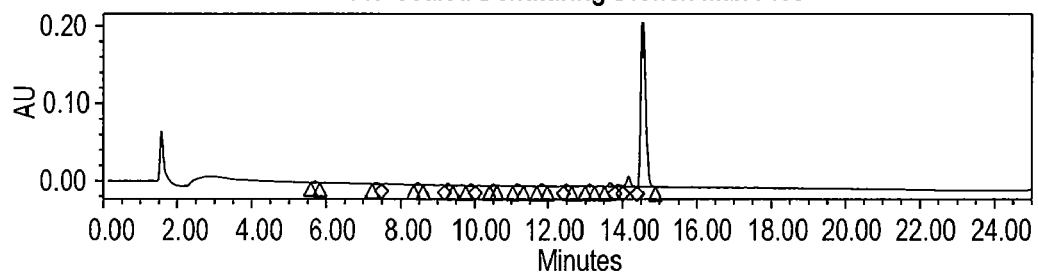
Fig. 7 - HPLC analysis of impurities retained
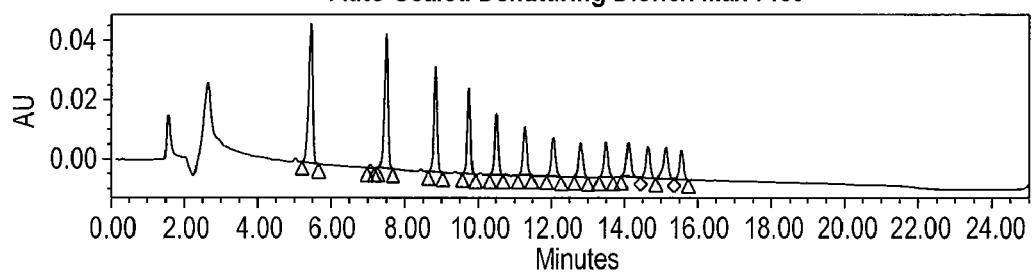
Fig. 8 - HPLC analysis of filtrate after NAP-10
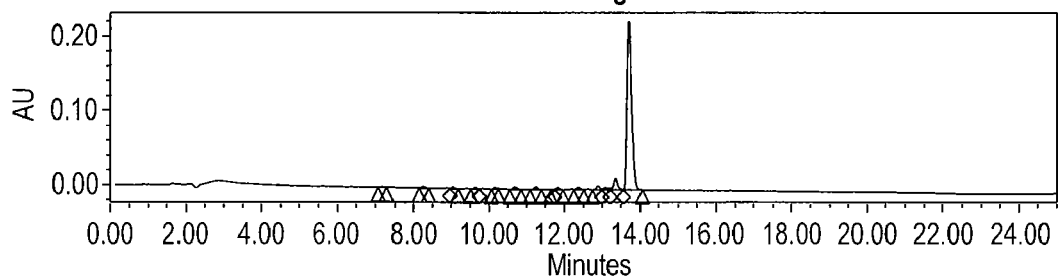

COMPOUNDS AND METHODS FOR SYNTHESIS AND PURIFICATION OF OLIGONUCLEOTIDES

CROSS-REFERENCE TO RELATED APPLICATIONS

This application claims priority to U.S. patent application No. 60/871,733, filed Dec. 22, 2006, which is incorporated herein by reference.

FIELD OF THE INVENTION

The invention relates generally to nucleic acid chemistry and molecular biology. More specifically, the invention provides methods of synthesizing and purifying nucleic acids in addition to chemical capping reagents, and compositions, kits and systems comprising such reagents. The invention may be used for a variety of industrial, medical and forensic purposes.

BACKGROUND OF THE INVENTION

The invention concerns new compounds and methods for the synthesis and purification of oligonucleotides, and more specifically, compounds and methods for synthesizing, chemically capping and purifying nucleic acids. Nucleic acids are of major importance in the living world as carriers and transmitters of genetic information. Since their discovery by F. Miescher they have aroused a wide scientific interest which has led to the elucidation of their function, structure and mechanism of action. Variations in nucleic acid sequence often account for differences in susceptibility to diseases and pharmacological responses to treatment. To illustrate, changes in a single base of a nucleic acid molecule, which are commonly referred to as single nucleotide polymorphisms (SNPs), can affect an individual's risk for a given disease. By comparing these variations, researchers are gaining an understanding of the medical utility of SNPs, thereby enhancing our ability to effectively diagnose, prognosticate, and treat disease. In addition, purified synthetic nucleotides are used for amplification in the polymerase chain reaction (PCR) and other amplification methods; as primers; hybridization probes for detection and/or sequencing, gene therapy, cloning, site-specific mutagenesis studies and the like. The quality of the result of these techniques is directly related to the purity of the oligonucleotides used.

As such, the purity of a nucleic acid molecule is crucial to elucidating the function and facilitating the manipulation of these molecules. Automated, solid phase synthesis is the most common approach for the production of short oligonucleotides. These synthetic methods are usually based on the stepwise reactions of phosphoramidite or H-phosphonate derivatives of nucleosides to form a continuous linkage of these monomeric building blocks in a pre-determined order (see e.g. T. Brown & D. J. S. Brown in Oligonucleotides and Analogues—A Practical Approach, (1991) (Eckstein, F., publ. IRL Press at Oxford University Press, Oxford, N.Y., Tokyo); Sambrook et al., 1989, *Molecular Cloning—A Laboratory Manual*, Cold Spring Harbor Laboratory, Cold Spring Harbor, N.Y.; *Oligonucleotide Synthesis* (M. J. Gait, ed., 1984); *Nucleic Acid Hybridization* (B. D. Hames and S. J. Higgins. eds., 1984); *Current Protocols in Nucleic Acid Chemistry*, Beaucage, S. L.; Bergstrom, D. E.; Glick, G. D.; Jones, R. A., Eds., John Wiley & Sons, Inc.: New York, Chapters 1-4, 2000-2004; and a series, Methods in Enzymology (Academic Press, Inc.). The resulting oligonucleotides, however, are heterogeneous mixtures of sequences, which complicates purification and limits the scale on which oligonucleotides can be made and the resulting yield. The problem of purification is further increased as the length of the strand increases. Typically the resulting unreacted 5'-hydroxyl groups are chemically capped with acetic anhydride to prevent further chain elongation with an incorrect "failure" sequence. Another method, which can be performed in parallel, is the so-called trityl-on purification (TOP) which utilizes the lipophilicity of the trityl protecting group. The desired sequence carrying the lipophilic trityl group is retained on a lipophilic support material while failure sequences lacking the trityl group are removed. Following cleavage of the trityl group under acidic conditions, the product of the desired sequence can be eluted from the lipophilic support.

A variety of methods are used to purify oligonucleotides—the above mentioned reversed-phase chromatography, anion-exchange (AX) chromatography, polyacrylamide gel electrophoresis (PAGE), ethanol precipitation, or a combination of these techniques. However, these methods have the disadvantage in that both the acyl and trityl groups are relatively labile to the conditions employed in oligonucletide synthesis (e.g. typical oligonucleotide deprotection conditions involve incubation in aqueous ammonia at 55-60° C. for 16 hours) resulting in poor purification or low yields. These methods are also limited in that the hydrophobic interactions are not particularly strong, so the isolation efficiency decreases rapidly with increasing chain length. Consequently, these methods are limited to producing nucleotides of less than 100 nucleotides with low yields of the desired sequence.

Fluorous affinity strategies have been used for the purification of peptides (see Filippov et al *Tetrahedron Lett.* 2002, 43: 7809-7812; de Visser et al; *Tetrahedron Lett* 2003 44: 9013-9016; Montanari et al. *J. Am. Chem. Soc.* 2004, 126: 9528; Brittain et al. *Nature Biotechnol.* 2005 23: 463-468; Markowicz et al. *Synthesis* 2004 80-86; Mizuno et al. *Chem. Lett* 2005 34: 426-427), oligosaccharides (see Palmacci et al. *Angew. Chem. Int. Ed* 2001, 40: 4433; Manzoni *Chem. Commun.* 2003, 2930-2931 and Goto et al *Synlett* 2004, 2221-2223). Fluorous affinity strategies have also been used for the purification of oligonucleotides (see Pearson et al. *J. Org. Chem.* 2005 70: 7114-7122; Beller *Helv. Chim. Acta* 2005, 88: 171-179; Berry et al. WO 2006/081035, U.S. Pat. Publication No. 2006/0178507) although these reports disclose only use of fluorous trityl groups. As mentioned above, acetate and trityl capping groups often do not survive the deprotection conditions typically employed in oligonucleotide synthesis. In addition, Berry et al. use fluorous-DMTr to tag full length material. Their fluorous-purified materials are a distribution of the full-length product plus the expected deletion oligonucleotides (i.e., n-1, n-2, etc.), since the final phosphoramidite coupling attached a fluorous-capped nucleotide to a preexisting distribution of the desired chain plus deletion materials, which are not resolvable by HPLC, but can be detected by capillary electrophoresis analysis.

The present invention solves these problems by providing a phosphorous-based fluorous affinity cap to cap failure sequences, a method which can be used independent of the nucleoside used. The method uses a combination of fluorous capping and fluorous affinity chromatography that results in high yields and purities of non-capped oligonucleotide that are free of failure sequences even with long (>15mer) oligomers.

BRIEF SUMMARY OF THE INVENTION

The above object is achieved by capping compounds of the general formula (I):

$$PR^1R^2R^3 \quad (I)$$

wherein $R^1$ is selected from the group consisting of $C_1$-$C_8$alkoxy-, $C_1$-$C_8$alkenyloxy- and $C_1$-$C_8$alkynyloxy-, optionally substituted with CN;

$R^2$ is halogen or $NR^4_2$;

$R^3$ has the formula -L-A;

each $R^4$ is $C_1$-$C_6$alkyl or are combined to form a 4 to 7 membered heterocyclic ring, optionally substituted with from 1 to 3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl;

L is $C_1$-$C_{10}$ alkyleneoxy-, which is optionally substituted with from 1-3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl-; and A is $C_1$-$C_{30}$ perfluoroalkyl.

In another aspect, the present invention provides a method of inhibiting extension of a oligonucleotide, comprising contacting an oligonucleotide with a capping reagent of formula (I).

In one embodiment, the present invention provides a method of preparing a modified oligonucleotide comprising X nucleotides wherein X is an integer of at least 3; the method comprising
 (a) contacting a plurality of oligonucleotides, each comprising X-n nucleotide or nucleoside units, with a modified nucleotide, wherein n is an integer from 1 to X-1; and
 (b) contacting unreacted product of (a) with a capping reagent of formula (I).

In another embodiment, the present invention provides a method of preparing an oligonucleotide comprising X monomeric units wherein X is an integer of at least 3; the method comprising
 (a) contacting a plurality of oligomers, each comprising X-n monomeric units with a monomer, wherein n is an integer from 1 to X-1;
 (b) contacting unreacted product of (a) with a capping reagent of formula (I); and
 (c) separating the non-capped oligomer from the remainder of the product of (b) by fluorous affinity chromatography.

In yet another embodiment, the present invention also provides a modified oligonucleotide comprising perfluoroalkyl groups produced by the methods of the present invention.

According to another embodiment, the present invention also provides an oligonucleotide comprising at least one modified nucleoside moiety comprising the formula:

$$Nu{\sim}OP(OR^3)(NR^4)$$

wherein Nu is a nucleoside;

$R^3$ has the formula -LA;

each $R^4$ is $C_1$-$C_6$alkyl or are combined to form a 4 to 7 membered heterocyclic ring, optionally substituted with from 1 to 3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl;

L is $C_1$-$C_{10}$ alkyleneoxy-, which is optionally substituted with from 1-3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl-;

A is $C_1$-$C_{30}$perfluoroalkyl; and

~indicates the point of attachment to a hydroxyl oxygen of the nucleoside.

In yet another embodiment, the present invention also provides compositions, kits and systems comprising the oligonucleotides and capping reagents of the present invention.

The foregoing and other features of the present invention will be understood with reference to the following description and accompanying drawings.

BRIEF DESCRIPTION OF THE DRAWINGS

FIG. 1 shows the solid-phase oligonucleotide synthesis cycle.

FIG. 2 shows the cleavage of the oligonucleotide from the solid support.

FIG. 3 shows the synthesis of a fluorous phosphoramidite capping reagent.

FIG. 4 illustrates fluorous-affinity purification.

FIG. 5 shows an HPLC analysis of crude fluorous-capped T-15 showing the presence of failure and correct sequences.

FIG. 6 shows an HPLC analysis of the product filtered through a FLUORO-PAK™ fluorous cartridge.

FIG. 7 shows an HPLC analysis of the impurities released from the column after filtration through a fluorous cartridge by washing the column with 40% acetonitrile in 0.1 M TEAA.

FIG. 8 shows an HPLC analysis of the filtrate after a NAP-10 desalting step.

DETAILED DESCRIPTION OF THE INVENTION

I. Definitions

Before describing the present invention in detail, it is to be understood that this invention is not limited to particular compositions or methods, which can, of course, vary. It is also to be understood that the terminology used herein is for the purpose of clarifying the description of particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

The term "a" or "an" refers to one or more; for example, a polymer refers to one or more polymers. As such, the terms "a" or "an" are used interchangeably herein.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

An "alkyl group" refers to a linear, branched, or cyclic saturated hydrocarbon moiety and includes all positional isomers, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2- dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described below. Substituents can be a variety of groups and include for example, R', -halogen, —OR', —NR'R", —SR', —SiR"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R"' each independently refer to hydrogen, unsubstituted $C_{1-8}$ alkyl, unsubstituted heteroalkyl, unsubstituted or substituted aryl, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substitutent =O (e.g., —C(O)CH$_3$, —C(O)CH$_2$CH$_2$OR' and the like). The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl and the like.

An "alkenyleneoxy group" refers to an alkenylene group that comprises an oxygen atom and includes, e.g., allyloxy, and the like.

An "alkynyleneoxy group" refers to an alkynylene group that comprises an oxygen atom and includes, e.g., propargyloxy, and the like.

The terms "arylalkoxy" refers to an aryl radical attached directly to an alkoxy group. For brevity, aryl as part of a combined term as above, is meant to include heteroaryl as well.

An "alcohol group" refers to an organic group that includes at least one hydroxy group.

A "halogen group" refers to a group that comprises a halogen atom, such as F, Cl, Br, or I.

"Haloalkyl" refers to alkyl group as defined herein in which one or more hydrogen atoms have been replaced with halogens, including perhaloalkyls, such as trifluoromethyl.

A "heterooligo" refers to an oligomer that comprises two or more different monomer residues.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2.sup.nd ed.; Wiley: New York, 1991). The following abbreviations refer to the indicated protecting groups. "Tr" refers to the compound Ph$_3$C, also known as triphenylmethyl, also known as trityl. "MMTr" refers to the compound (4-CH$_3$OPh)C(Ph)$_2$, also known as monomethoxytrityl. "DMTr" refers to the compound (4-CH$_3$OPh)$_2$CPh, also known as dimethoxytrityl. "TBDMS" refers to the compound t-butyldimethylsilyl. "TES" refers to the compound triethylsilyl. "TIPS" refers to the compound triisopropylsilyl. "Boc" refers to the compound (CH$_3$)$_3$CO$_2$C, also known as t-butyloxycarbonyl. "Cbz" refers to the compound PhCH$_2$O$_2$C, also known as benzyloxycarbonyl. "Piv" refers to the compound (CH$_3$)$_3$CO, also known as pivaloyl.

The term "plurality" refers to more than one; for example, a plurality of polymers refers to two or more polymers.

As used herein, the terms, "oligomers" and "polymers" refer generally to molecules that are made by linking together repeating units of one or more small molecules called monomers. Generally, oligomers include fewer monomer units than polymers, although the precise border between an oligomer and a polymer in not well defined and for the purposes of this invention the terms are used interchangeably to encompass the full scope of both terms. The oligomers may have differing numbers of repeat units. The oligomers may be attached to tags or labels.

A "sequence" of a nucleic acid refers to the order and identity of nucleotides in the nucleic acid. A sequence is typically read in the 5' to 3' direction.

The term "monomer" refers to a compound capable of being polymerized. The term "monomeric unit" refers to units which are repeated in a polymer.

The term "nucleic acid" refers to nucleotides (e.g., ribonucleotides, deoxyribonucleotides, dideoxynucleotides, etc.) and polymers (e.g., "oligonucleotides") comprising deoxyribonucleoic acids (DNAs), ribonucleic acids (RNAs), DNA-RNA hybrids, oligonucleotides, polynucleotides, genes, cDNAs, aptamers, antisense nucleic acids, interfering RNAs (RNAis), molecular beacons, nucleic acid probes, peptide nucleic acids (PNAs), PNA-DNA conjugates, PNA-RNA conjugates, etc.) that comprise such nucleotides covalently linked together, either in a linear or branched fashion. An oligonucleotide is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321), O-methylphosphoroamidite linkages (see Eckstein, Oligonucleotides and Analogues: A Practical Approach, Oxford University Press (1992)), and peptide nucleic acid backbones and linkages (see, Egholm (1992) *J. Am. Chem. Soc.* 114:1895; Meier et al. (1992) *Chem. Int. Ed. Engl.* 31:1008; Nielsen (1993) *Nature* 365:566; Carlsson et al. (1996) *Nature* 380:207), which references are each incorporated by reference. Other analog nucleic acids include those with positively charged backbones (Denpcy et al. (1995) *Proc. Natl. Acad. Sci. USA* 92: 6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) *Chem. Soc. Rev.* pp. 169-176, which is incorporated by reference). Several nucleic acid analogs are also described in, e.g., Rawls, *C & E News* Jun. 2, 1997 page 35, which is incorporated by reference. These modifications of the ribose-phosphate backbone may be done to facilitate the addition of additional moieties such as labels, or to alter the stability and half-life of such molecules in physiological environments. In addition to the naturally occurring heterocyclic bases that are typically found in nucleic acids (e.g., adenine, guanine, thymine, cytosine, and uracil), nucleic acid analogs also include those having non-naturally occurring heterocyclic bases. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., Seela et al. U.S. Pat. No. 5,990,303, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

An "oligonucleotide" refers to a nucleic acid that includes at least two nucleotides, typically more than three nucleotides, and more typically greater than ten nucleotides. The exact size of an oligonucleotide generally depends on various factors, including the ultimate function or use of the oligonucleotide. As used herein the term "oligonucleotide" refers to a single stranded chain of either nucleotides or chemical modifications thereof, such as e.g. nucleotides with a 2'O-4'C-methylene bridge in their sugar portion, which are the nucleotides that make up locked nucleic acids (LNA). Modifications include, but are not limited to, those that provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, bases that can be part of unusual base-pairing combinations such as the isobases isocytidine and isoguanidine and the like. Modifications further include attached labels and reporter molecules, such as fluorescent dyes, biotin, minor groove binders and the like that are known to those skilled in the art. In addition modifications include modified backbones of the oligonucleotides, examples being peptide nucleic acids (PNA), phosphorothioate DNA, methylphosphonate DNA and other modifications known to those skilled in the art as reviewed by Micklefield (2001) Current Medicinal Chemistry 8:1157-1179, which is specifically incorporated herein by reference in its entirety. Oligonucleotides, as referred to in this invention, can consist of any combinations of the nucleotides and their modifications described above and can have either a few, e.g. up to 20, or many, e.g. 20 to several hundred or more, nucleotides incorporated in their chain, the total number of nucleotides being denoted n in the context of this invention.

The terms "failure sequence", "contaminant polymer" and "contaminant derivatives" are used interchangeably to refer to those polymers formed during polymer synthesis that are not comprised of the desired number and/or the desired sequence of monomers. These therefore represent impurities in the synthesized polymers. Failure sequences are typically capped in polymer synthesis and thereby converted to truncated sequences. Failure sequences comprise contaminant derivatives as defined herein with chain lengths from 1 to X-1, wherein X is an integer of at least 3.

"Capping" and "capping step" as used herein refer to reacting the free hydroxyl group, or any other functional group suitable for chain extension, of a polymer e.g. an oligonucleotide chain with a capping reagent during solid phase polymer synthesis to render the chain incapable of participating in subsequent coupling steps. For oligonucleotide synthesis, capping can be performed either on the 5'-functional group of a 3' to 5' extended oligonucleotide or on the 3'-functional group of a 5' to 3' extended oligonucleotide. Capping steps are performed in between the coupling step of the solid phase polymer synthesis and the next deprotection step. The capping reagents of the embodiments of this invention comprise functional groups that allow the post-synthetic removal of contaminant polymers, as defined below.

As used herein, the terms "cap" or "capping group" refers to the chemical group which is introduced on a failure sequence during a capping step in polymer synthesis that prevents the extension of a polymer, e.g. nucleic acid to which it is attached. To illustrate, phosphoramidite blocking groups at the 5'-positions of nucleotides of the invention include fluorous groups. Representative capping groups and capped monomers are also described further herein.

"Affinity" refers to the association of contaminant polymer to a solid phase, herein denoted "affinity support". The term "affinity" as used herein refers to a solid phase that is derivatized with a moiety capable of forming a strong association with a corresponding functional group introduced to the contaminant polymer via capping. In the case of fluorous affinity chromatography, the solid phase may be derivatized with fluorous moieties. Said derivatizations are accomplished by attaching said moieties to functional groups on the solid phase. These functional groups include, but are not limited to, polyfluoroalkanes and the like.

A "solid phase" as used herein refers to a resin, membrane or polymer that is insoluble in the medium employed in a particular reaction or unit operation performed to synthesize or purify polymers of the invention. A solid phase can be of inorganic nature, including, but not limited to inorganic oxides such as silica, alumina, zeolites and controlled pore glass (CPG), or of organic nature, including, but not limited to polystyrene-divinylbenzene, polyacrylamide, polymethacrylate, polyvinylalcohol, other synthetic polymers, carbohydrates such as cellulose and starch or other polymeric carbohydrates, or other organic polymers and any copolymers, composite materials or combination of the above inorganic or organic materials. Furthermore, a solid phase can be comprised of a soluble polymer that can be forced to undergo a phase transition, e.g. polyethylene glycol and derivatives thereof, as described e.g. by Bayer et al. (1972) *Nature* 237: 512-513, which is incorporated herein by reference in its entirety.

"Extended" refers to a polymer e.g. a nucleic acid to which one or more additional monomers, e.g. nucleotides, have been added or otherwise incorporated (e.g., covalently bonded to). Nucleic acids are "extended" or "elongated" when additional nucleotides (or other analogous molecules) are incorporated into the nucleic acids. For example, a nucleic acid may be extended by a nucleotide incorporating biocatalyst, such as a polymerase that typically adds nucleotides at the 3' terminal end of a nucleic acid. A nucleic acid may also be extended by a chemical reaction, e.g., a DNA synthesis reaction.

"Extendible" refers to a polymer, e.g. an oligo- or polynucleotide to which at least one other monomer, e.g. a nucleotide can be added or covalently bonded, e.g., in a DNA synthetic reaction or in a reaction catalyzed by a monomer incorporating biocatalyst.

"Non-extendible" refers to a polymer, e.g. an oligo- or polynucleotide which is blocked from further extension, i.e., no more nucleotides can be added or covalently bonded, e.g., in a DNA synthetic reaction or a reaction catalyzed by a monomer-incorporating biocatalyst.

The term "capped" refers to a feature of a monomer or oligomer, e.g. a nucleotide or oligonucleotide that comprises a capping group. For nucleotides this is usually at the 5'-position or the 3' position of the sugar moiety of the nucleotide.

The term "lipophilic" or "lipophilicity" typically refers to a tendency of hydrocarbon groups to associate, based on the increase in entropy of the solvent in which they are in. This effect is especially pronounced in water wherein this interaction is termed "hydrophobic".

The term "fluorous" refers to a highly fluorinated organic moiety. The moieties may be linear or branched $C_1$-$C_{30}$perfluoroalkyl groups. The related term "perfluoroalkyl/fluorous affinity handle" is employed herein to refer to a ligand of a capping reagent bearing one or more fluorous groups, and additionally to entire oligonucleotides synthesized with such reagents, and so bearing one or more such fluorous groups. The term "fluorous interacation" refers to the tendency of fluorinated molecules to associate with other fluorinated substances. Fluorous interactions are generally stronger than lipophilic interactions allowing for smaller caps to be used to more effectively separate longer molecules.

The term "hydrocarbon" refers to a moiety consisting of carbon and hydrogen atoms. Examples of hydrocarbons include, but are not limited to, alkyl groups, alkenyl groups, alkynyl groups, aryl groups, arylalkyl groups, arylalkenyl groups, arylalkynyl groups and the like.

A "moiety" or "group" refers to one of the portions into which something, such as a molecule, is divided (e.g., a functional group, substituent group, or the like). For example, a nucleotide typically comprises a basic group (e.g., adenine, thymine, cytosine, guanine, uracil, or an analog basic group), a sugar moiety, and one or more phosphate groups.

A "heterocyclic ring" refers to a monocyclic or polycyclic ring that is either saturated, unsaturated, or aromatic, and which comprises one or more heteroatoms independently selected from nitrogen, oxygen and sulfur. A heterocyclic ring may be attached to the sugar moiety, or analog thereof, of a nucleotide of the invention via any heteroatom or carbon atom. Exemplary heterocyclic rings include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl, and the like.

A "full-length sequence" refers to a nucleic acid sequence that comprises at least substantially the same number of nucleotides as a reference sequence or a nucleic acid sequence that is at least partially complementary to the reference sequence. In certain embodiments of the invention, for example, an extended primer nucleic acid is complementary to a full-length sequence of a template nucleic acid or other reference sequence.

The term "attached" refers to interactions including, but not limited to, covalent bonding, ionic bonding, chemisorption, physisorption, and combinations thereof.

A "linker" refers to a chemical moiety that covalently or non-covalently (e.g., ionically, etc.) attaches a compound or substituent group to, e.g., a solid support, another compound or group, or the like. For example, a linker may attach a label (e.g., a fluorescent dye, a radioisotope, etc.) to a nucleotide or the like. Linkers are typically bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support, another compound, etc. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Additional description of linker molecules is provided in, e.g., Lyttle et al. (1996) *Nucleic Acids Res.* 24(14):2793, Shchepino et al. (2001) *Nucleosides, Nucleotides, & Nucleic Acids* 20:369, Doronina et al (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, and Pljevaljcic et al. (2003) *J. Am. Chem. Soc.* 125(12):3486, which are each incorporated by reference.

A "label" or "tag" refers to a moiety attached (covalently or non-covalently), or capable of being attached, to a molecule, which moiety provides or is capable of providing information about the molecule (e.g., descriptive, identifying, etc. information about the molecule). Exemplary labels include fluorescent labels, weakly fluorescent labels, non-fluorescent labels, calorimetric labels, chemiluminescent labels, bioluminescent labels, radioactive labels, mass-modifying groups, antibodies, antigens, biotin, haptens, and enzymes (including, e.g., peroxidase, phosphatase, etc.).

II. Introduction

Turning now to the following written specification and the drawings, the present invention provides phosphorous-based fluorous oligonucleotide capping reagents, as well as a methodology for the purification of uncapped, target oligonucleotides using separation media having greater affinity for those fluorous capped oligonucleotides which are unwanted by-products, such as, for instance, failure and deletion sequences, etc. of an oligonucleotide chemical synthesis reaction.

III. Oligonucleotide Synthesis by Single Nucleotide Extensions

The present invention relates generally to methods for capping and/or blocking the extension of polymers, e.g. oligonucleotides, utilizing a capping reagent or a capped monomer. With regard to oligonucleotides the method comprises (a) contacting a plurality of oligonucleotides with a modified nucleotide or nucleoside; and (b) contacting unreacted product of (a) with a capping reagent comprising a perfluoroalkyl affinity handle.

Typically, the olignucleotide to be synthesized comprises at least 3 monomeric units.

In other embodiments, the oligomers are attached to a solid support for steps (a) and (b). In other embodiments, the oligomers are cleaved from the solid support before step (c) wherein the non-capped oligomers of the desired target sequence are separated from capped truncated oligomers of by fluorous affinity methodology. Examples of solid supports suitable for the present invention include, but are not limited to, glass, typically a derivatized controlled pore glass (CPG); silica, alumina, zeolite, synthetic polymers or copolymers such as polystyrene; combinations thereof and the like.

The methods and compositions of the present invention are suitable for use in the synthesis and purification of a wide variety of polymers or oligomers. In some embodiments, the invention provides compositions and methods for the synthesis and purification of biopolymers. In one embodiment, the oligomer is an oligonucleotide, which will be used to illustrate the present invention.

The synthesis of oligonucleotides on solid phase can be done using standard techniques well known in the art, for example, the phosphoramidite method of Beaucage et al., 1981, *Tetrahedron Lett.* 22:1859-1862; and the solid support method of U.S. Pat. No. 4,458,066; T. Brown & D. J. S. Brown in Oligonucleotides and Analogues—A Practical Approach, (1991) (Eckstein, F., publ. IRL Press at Oxford University Press, Oxford, New York, Tokyo); McBride and Caruthers (1983) *Tetrahedron Letters* 24:245-248 and Sinha et al. (1983) *Tetrahedron Letters* 24:5843-5846, the phosphotriester method of Narang et al. (1979) *Meth. Enzymol.* 68:90-99; the phosphodiester method of Brown et al. (1979) *Meth. Enzymol.* 68:109-151; the phosphoramidite method of Matteucci et al. (1981) *J. Am. Chem. Soc.* 103:3185-3191; among other methods known in the art, which references are each incorporated by reference. Such methods of synthesis are based essentially on the stepwise reaction of phosphoramidites or H-phosphonates and the continuous linkage of these monomeric building blocks to form oligomers. To illustrate, FIG. 1 depicts the synthesis cycle of an oligonucleotide that produces a mixture of an oligonucleotide with a correct sequence and capped oligonucleotides with incorrect or failure sequences in various ratios according to certain embodiments of the invention. Nucleotides can be extended via the hydroxyl group at either the 3'- or 5'-position of an intact sugar ring (e.g., pentose sugar ring) or a sugar analog ring (e.g., carbocyclic ring, etc.). For purposes of illustration only, FIG. 1 shows the synthesis is carried out in the 3' to 5' direction by adding nucleotides to the 5' end of the growing chain. Further, while FIG. 1 only shows the extension and capping of a pair of monomers, the present invention is not limited by the number or size of the nucleic acids being synthesized or purified. Synthesis in this direction is carried out using nucleotide phosphoramidites in which the phosphoramidite group is attached to the 3'-oxygen and a protecting or blocking group (e.g., a negatively charged blocking group, a bulky blocking group, and/or the like).

In the solid support method, an initial nucleotide is coupled to the solid support. The oligonucleotide is extended by the sequential addition of nucleotides until the desired sequence is obtained. The sequential extension involves the following steps:

1. removing a protecting group from the partially synthesized, support-bound oligonucleotide chain to generate a reactive hydroxyl group;
2. coupling a nucleotide to the support-bound oligonucleotide chain through a phosphite linkage;
3. oxidizing the phosphite linkage to yield a phosphate linkage; and
4. capping unreacted hydroxyl groups on any support-bound oligonucleotides not extended.

Initially, the 5'-hydroxyl of the nucleotide 1a and 1b is also blocked or protected with a suitable protecting group which can be selectively removed. Examples of suitable protecting groups, include, but are not limited to trityl groups, such as 4,4'-dimethoxytrityl (DMT), silyl groups, such as t-butyldimethylsilyl (TBDMS); acyl groups, such as t-butoxycarbonyl (BOC), and the like. When synthesized in this direction, the product obtained prior to removal of the final protecting group is an oligonucleotide with a protecting group attached to the 5' terminus.

Alternatively, oligonucleotide synthesis can be carried out in the 5' to 3' direction by adding nucleotides to the 3' end of the growing chain. Synthesis in this direction is carried out using nucleotide phosphoramidites in which the phosphoramidite group is attached to the 5'-oxygen and a protecting group, again typically a dimethoxytrityl group, is attached to the 3'-oxygen. When synthesized in this direction, the product obtained prior to removal of the final protecting group is an oligonucleotide with a protecting group attached to the 3' terminus.

Synthesis in the 5' to 3' direction provides a convenient method of synthesizing an oligonucleotide with a blocking group attached to the 3' terminal oxygen. Omission of a deprotection step following addition of the final nucleotide to the oligonucleotide chain results in the synthesis of an oligonucleotide with a protecting (i.e., blocking) group attached to the 3' terminal oxygen.

In the deblocking or deprotecting step the 5'-hydroxyl protecting group is removed to form a compound with a free 5'-hydroxyl 2a and 2b. The conditions to remove a particular protecting group depend on the protecting group used. In the case of DMT, this can be done by adding an acid, such as dichloroacetic acid (DCA) or trichloracetic acid (TCA) in dichloromethane.

In the coupling or nucleotide condensation step the 5'-hydroxyl of 2a and 2b is coupled with an activated nucleotide 2c to form the extended nucleotide of a particular sequence. Activation of the nucleotide can be accomplished by using a nucleoside phosphoramidite in the presence of a tetrazole compound which then combines with the 5'-hydroxyl of the first nucleotide to form a phosphite linkage 3a.

Subsequent oxidation converts the phosphate linkage of 3b to the phosphate linkage of 4b. Examples of oxidation conditions include dilute aqueous iodine in pyridine and tetrahydrofuran.

Irrespective of the method used, in each synthetic cycle there is a capping step in which a cap is introduced to unreacted terminal functional groups of the growing oligonucleotide chain which failed to be extended in the preceding coupling step 2a. The unextended nucleotides are capped 3a so that they may no longer react in subsequent sequence extension cycles to form oligos with deletion sequences.

While not limiting, capping during oligonucleotide synthesis may be done by passing a capping reagent, comprising a mixture of acetic anhydride and N-methylimidazole in THF/pyridine, through the column at the end of each coupling cycle. Various basic compounds can be used to adjust the pH of the reaction mixture including, but not limited to KOH, NaOH, and the like among many others that are widely known in the art. The nucleotide is typically the limiting reagent. Although other temperature conditions are optionally utilized, these synthesis reactions are generally performed at or near room temperature. While not limiting, these reactions are generally allowed to proceed for about 100 to 500 seconds.

It is possible to perform the capping step before the oxidation step. Each of these steps is then repeated until an oligonucleotide of the desired sequence has been synthesized.

Following the last extension step, the oligonucleotide is cleaved from the solid support according to standard techniques of solid-phase oligonucleotide synthesis known in the art. For example as shown in FIG. 2, this can be done by incubating the product in a base, including, but not limited to ammonia, ammonium hydroxide and the like for about 6 to 24 hours. The crude product is a mixture of the desired oligonucleotide, failure sequences, cleaved groups and reaction solutions. The terminal protective group of the oligonucleotide 5b may or may not be removed within this step. The caps of the present invention are designed such that they are stable during the synthesis and the work-up of the oligonucleotide.

From this, a mixture of the full-length oligonucleotide product 5b and failure/contaminant truncated sequences 4a are obtained. Following cleavage from the solid support the reaction mixture is concentrated at least partially or completely under reduced pressure to remove solvents and volatile reagents. In certain embodiments, a suitable aqueous buffer may be added to the residual solution or to the solid residue of the polymer product mixtures. The partially concentrated solution or solid residue thus obtained can be purified as described in more detail below.

Preferably, the synthesis reaction is carried out in a commercially available automated DNA synthesizer (e.g., ABI 394 DNA synthesizer from Applied Biosystems, Foster City, Calif.) using commercially available nucleoside phosphoramidites (e.g., from Glen Research, Sterling, Va.). Nucleoside phosphoramidites usable for synthesis in the 5' to 3' direction, which contain a dimethoxytrityl group attached to the 3' oxygen, are also commercially available from Glen Research (Sterling, Va.).

The synthesis of exemplary capped oligomers is described in the examples. Additional capped oligomers can be synthesized using standard synthesis methods in an analogous manner.

Thus in one group of embodiments, the invention provides a method of preparing a modified oligonucleotide comprising X nucleotides or nucleosides wherein X is an integer of at least 3; the method comprising (a) contacting a plurality of oligonucleotides, each comprising X-n nucleotide or nucleoside units, with a modified nucleotide or nucleoside, wherein n is an integer from 1 to X-1; and (b) contacting unreacted product of (a) with a capping reagent comprising a perfluoroalkyl affinity handle. In another group of embodiments, the solid support is selected from the group consisting of glass, silica, alumina, zeolite, synthetic polymers or copolymers and combinations thereof. In another group of embodiments, the modified nucleotide is a protected nucleotide. In another group of embodiments, the oligonucleotide is prepared 3' to 5'. In another group of embodiments, the oligonucleotide is prepared 5' to 3'. In another group of embodiments, the capping reagent is one of the embodiments described herein.

IV. Capping Reagents

In addition, the invention also provides capping reagents and methods of producing capping reagents. The caps comprise a fluorous affinity handle that can be retained by fluorous affinity chromatography such that oligomers consisting of between about 4 and 100 or more monomers. In various groups of embodiments, 4, 10, 20, 30, 40, 50, 60, 70, 80, 90, 100 or greater than 100 monomers can be purified from shorter failures sequences. Examples of such affinity handles include, but are not limited to, perfluoroalkyl groups. Thus in one embodiment of the present invention the cap is derivatized with a fluorous moiety capable of binding to a fluorous affinity support. When fluorous-based affinity purification is performed then a fluorous cap is coupled to the failure sequences, allowing for the failure sequences to be selectively retained on the fluorous affinity support.

The affinity handle can be attached to a variety of capping functionalities, including but not limited to a phosphoramidite or a chlorophosphite.

Accordingly, in one embodiment of the present invention fluorous-based affinity purification is used in an oligonucleotide synthesis reaction. Within this embodiment, a phosphorous-based fluorous capping reagent is used. A phosphorous-based fluorous capping reagent according to the present invention generally is described by the formula (I):

wherein $R^1$ is selected from the group consisting of $C_1$-$C_8$alkyloxy-, $C_1$-$C_8$alkenyloxy- and $C_1$-$C_8$alkynyloxy-, optionally substituted with CN;

$R^2$ is halogen or $NR^4{}_2$;

$R^3$ has the formula -L-A;

each $R^4$ is $C_1$-$C_6$ alkyl or are combined to form a 4 to 7 membered heterocyclic ring, optionally substituted with from 1 to 3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl;

L is $C_1$-$C_{10}$alkyleneoxy-, which is optionally substituted with from 1-3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl-; and A is $C_1$-$C_{30}$perfluoroalkyl.

In certain embodiments, $R^1$ is —$OCH_3$. In another group of embodiments, $R^1$ is —$O\ CH_2CH=CH_2$. In another group of embodiments, $R^1$ is —$OCH_2CH_2CN$.

In certain embodiments, $R^2$ is a halogen. In another group of embodiments, $R^2$ is selected from the group consisting of —$N(Me)_2$, —$N(Et)_2$, —$N(Pr)_2$, —$N(i$-$Pr)_2$, 1-pyrrolidnyl, 1-piperidinyl, 4-morpholinyl and 1-imidazolyl. In another group of embodiments, $R^2$ is —$N(i$-$Pr)_2$.

In certain embodiments, $R_3$ has the formula —O—$(CH_2)_m$$(CF_2)_p CF_3$; m is between about 1 and about 30. In various groups of embodiments, m is 1, 2, 3, 4, 5, 6, 7, 8, 9 or 10 and p is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In another group of embodiments, m is 3 and p is 7.

The capping compounds according to the invention can be synthesized in various ways. In some cases one can start with commercially available precursors. FIG. 3 illustrates the synthesis of a phosphorous-based fluorous capping reagent of the present invention. In addition, FIG. 3b shows a step in a synthesis of 2-cyanoethyl-N',N'-diisopropyl 3-perfluoroalkyl-propyloxy-phosphoramidite according to one embodiment of the invention. Perfluoroalcohols, such as 3-(perfluorooctyl)propanol and 3-(perfluorohexyl)propanol are commercially available from companies such as Fluorous Technologies, Inc. (Pittsburgh, Pa.). Halophosphoramidites, such as 2-cyanoethyl disopropylchlorophosphoramidite, are commercially available from companies such as Sigma-Aldrich, Inc. (St Louis, Mo.).

The use of the compounds according to the invention to cap nucleic acids and provide a handle which allows for the purification of nucleic acids of a desired sequence has proven to be particularly advantageous, especially compared to the classical capping reagents such as acetic anhydride. One advantage is chemical stability under a wide range of pH conditions. Another advantage of the present method is that it allows for an easy separation of the full-length oligonucleotide away from failure sequences. Because of the efficiency of the purification the full length oligonucleotide may be obtained in high yield and purity.

Additional synthetic pathways and other aspects related to the production of the capping reagents of the invention are provided in the examples below. Various synthetic techniques can be adapted for use in the synthesis protocols of the present invention, examples of which are generally known and described in, e.g., March, Advanced Organic Chemistry: Reactions, Mechanisms, and Structure, 4$^{th}$ Ed., John Wiley & Sons, Inc. (1992), and Carey and Sundberg, Advanced Organic Chemistry Part A: Structure and Mechanism, 4th Ed., Plenum Press (2000), which are each incorporated by reference. Chemical starting materials and other reaction components useful in the synthesis of the capping reagents of the present invention are readily available from various commercial suppliers including, e.g., Sigma-Aldrich, Inc. (St Louis, Mo.) and Fluorous Technologies, Inc. (Pittsburgh, Pa.).

The capping reagents can be purified prior to use by a variety of separation techniques including, but not limited to, liquid chromatography, and the like. Various separation techniques that are useful or may be adapted in purifying capping reagents are described further in, e.g., Skoog et al., Principles of Instrumental Analysis, 5$^{th}$ Ed., Harcourt Brace College Publishers (1998) and Currell, Analytical Instrumentation: Performance Characteristics and Quality, John Wiley & Sons, Inc. (2000), which are both incorporated by reference.

V. Fluorous Affinity Purification of Oligonucleotides

In fluorous affinity, molecules containing perfluoroalkyl or fluorous groups are purified using their affinity for perfluorinated media. Fluorous affinity interactions are strong and distinquishable from other types of affinity interactions (e.g. lipophilicity). Thus in one embodiment, oligomers of the correct sequence can be purified from failure sequences by capping the failure sequences with a fluorous capping group and then employing a fluorous separation technique to separate the capped molecules from oligomers of the correct sequence. Examples of fluorous separation techniques, include but are not limited to, fluorous affinity chromatography such as high performance liquid chromatography (HPLC), solid phase extraction ("SPE" or "cartridge purification") on fluorous reversed-phase silica-gel (FRPSG) (see e.g., liquid phase extraction) filtration and the like.

Turning now to FIG. 4, the oligonucleotide purification methodology of the instant invention is generally depicted schematically to comprise the following ordered steps. Thus after the oligonucleotide is prepared as described above by (a) contacting the oligonucleotides, with a modified nucleotide or nucleoside; and (b) contacting unreacted product of (a) with the capping reagent comprising a perfluoroalkyl affinity handle, the oligonucleotide is purified by: (c) separating the non-capped oligomers of the desired target sequence from capped truncated oligomers of (b) by fluorous affinity methodology. In another group of embodiments, the plurality of oligomers are attached to a solid support for steps (a) and (b) and cleaved from the solid support before step (c).

More particularly, and with continuing reference to FIG. 4, the heterogenous mixture of oligonucleotide synthesis products and reagents, including the fluorous-capped failure sequence oligonucleotide 4a, is passed through a cartridge or column containing an adsorbent or media that bears fluorous affinity groups on a solid support, leading to the capture of the fluorous-capped oligonucleotide failure sequences to yield the complex 5a. The undesired materials having a fluorous-capped oligonucleotide 4a, interact with the adsorbent, so that washing the adsorbent with at least a first suitable solvent allows the desired non-capped oligonucleotide 5b to elute, leaving only the complex 5a. Dissociation of the undesired fluorous-capped oligonucleotides 5b from the adsorbent may then be accomplished by washing with a second, more fluorophilic solvent. In cases where the fluorous-capped failure sequence oligonucleotides are retained, the non-capped oligonucleotide 5b is the final purified target compound.

Thus, in another group of embodiments, the purifying comprises:

(i) passing the product of step (b) through a fluorous affinity medium such that the capped oligomers are adsorbed by said fluorous affinity medium; and (ii) washing the non-capped oligomers of the desired target sequence from the fluorous affinity medium.

In other embodiments, more than one fluorous group may be employed in any of the reagents disclosed in this specification if more demanding affinity interactions are required with the separation medium employed in subsequent purification. This can be accomplished by attachment of more than one fluorous group to the phosphorous scaffold, or by using a linker that accommodates one or more branched fluorous chains.

The separation medium comprises any groups demonstrating a strong interaction with the fluorous-group of the oligonucleotide reagents of the present invention. Thus, in one embodiment the separation medium may take the form of conventional lipophilic reverse-phase adsorbents based on a matrix of silica, poly(divinylbenzene) or polystyrene cross-linked with divinylbenzene. In other embodiments the separation medium comprises a reverse-phase adsorbent bearing fluorinated groups, including, for example, a polymeric (such as, for instance, poly(divinylbenzene) or polystyrene cross-linked with divinylbenzene) or silica matrix bearing fluorinated organic groups. Exemplary alternate adsorbents include FLUOROFLASH (Fluorous Technologies, Inc.), a silica-based material bearing fluorinated groups, and POLY-PAK (Glen Research Corporation) and OPC (Applied Biosystems, Inc.) cartridges, which use polymeric reverse-phase adsorbents, although in practice, any solid or liquid-phase bearing fluorophilic groups may be used.

VI. Nucleotides and Nucleotide Compositions

The invention also provides nucleotides, oligonucleotides and other compositions, e.g. reagent solutions and reaction mixtures, that comprise at least one capping reagent or moiety as described herein. In some embodiments, the invention provides a modified nucleoside moiety comprising the formula:

Nu~PO$_3$R$^3$ wherein Nu is a nucleoside;

R$^3$ has the formula -LA;

L is $C_1$-$C_{10}$ alkyleneoxy, which is optionally substituted with from 1-3 substituents selected from the group consisting of $C_1$-$C_6$alkyl-, $C_1$-$C_6$haloalkyl-, $C_1$-$C_6$alkoxy-arylC$_1$-$C_6$alkoxy-, oxo- and $C_1$-$C_6$alkoxycarbonyl-;

A is $C_1$-$C_{30}$perfluoroalkyl; and

 indicates the point of attachment to a hydroxyl oxygen of the oligonucleotide. In some embodiments, the nucleoside may include conventional protecting groups. More specific examples of such alternative reagents—that is, nucleoside reagents comprising at least one permanently incorporated fluorous group—are provided herein. In other embodiments, the invention provides an oligonucleotide produced by the methods described herein.

In some embodiments, the compositions may also include a solid support to which the modified nucleoside or oligonucleotide is optionally attached. Examples of solid supports include, but are not limited to, glass, silica, alumina, zeolite, synthetic polymers or copolymers and combinations thereof. In some embodiments, the invention provides a reagent solution comprising at least one capping reagent as described herein. In other embodiments, the invention provides a reaction mixture comprising at least one capping moiety as described herein. Within these embodiments, the compositions may further include at least one of: (a) at least one solvent; (b) at least one extendible monomer, e.g. a nucleotides or a modified nucleotide; (c) at least one catalyst; and (d) at least one buffer. The ratio of capping reagent or moiety to the other component(s) in the composition depends on the nature of the other component(s) of the composition and the method for making the composition. Further non-limiting examples of compositions of the invention are provided in the examples.

VIII. Kits

The present invention also provides kits for example for the synthesis and purification of oligonucleotides The kits include as a component at least one capping reagent as described herein. In some embodiments, the kit further includes one or more of: (a) at least one extendible monomer, e.g. a nucleotides or a modified nucleotide or a phosphoramidite; (b) at least one solid support; (c) at least one catalyst for use in extending the oligonucleotides; (d) at least one buffer; (e) at least one set of instructions for extending the oligonucleotides, e.g. nucleic acid, using with the components of the kit; and (f) at least one a container for packing the components of the kit.

The following experimental examples further demonstrate the foregoing methodology using fluorous-capped oligonucleotide reagents as described elsewhere herein.

The following examples are offered by way of illustration only and are not intended to limit the scope of the claimed invention. Numerous embodiments of the invention within the scope of the claims that follow the examples will be apparent to those of ordinary skill in the art from reading the foregoing text and following examples.

EXAMPLES

General Analytical Methods

All TLC analyses were performed using EM Science #5715-7, Silica Gel 60 F$_{254}$, 0.25 mm thickness TLC plates. All GC chromatograms were obtained using an HP5890 Series II Gas Chromatograph with FID detector and an Agilent #19091Z-413, HP-1, 30 m×0.32 mm, 25 micron column. All NMR spectra were obtained using a Bruker 270 MHz NMR.

Example 1

Preparation of Capping reagent 1: 2-cyanoethyl-N'N'-diisopropyl 3-perfluorhexyl-propyloxy-phosphoramidite

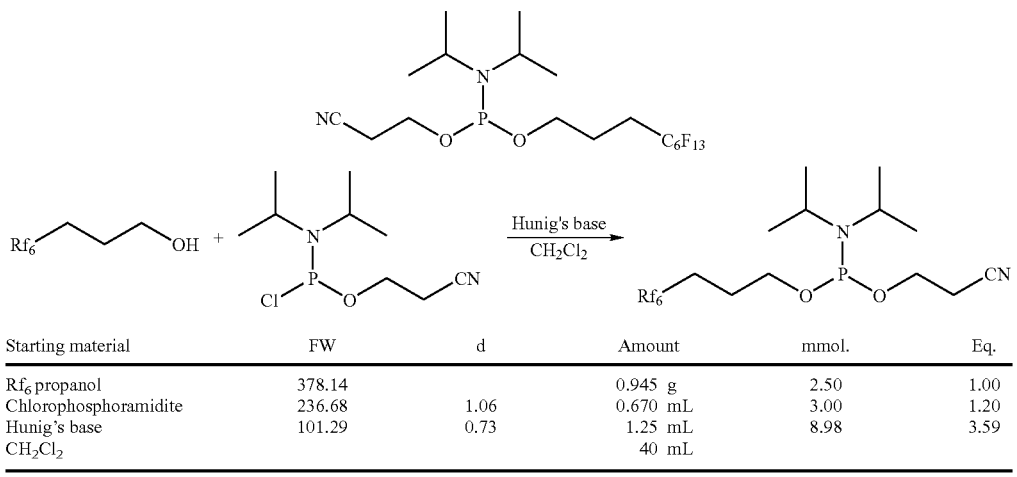

| Starting material | FW | d | Amount | mmol. | Eq. |
|---|---|---|---|---|---|
| $Rf_6$ propanol | 378.14 | | 0.945 g | 2.50 | 1.00 |
| Chlorophosphoramidite | 236.68 | 1.06 | 0.670 mL | 3.00 | 1.20 |
| Hunig's base | 101.29 | 0.73 | 1.25 mL | 8.98 | 3.59 |
| $CH_2Cl_2$ | | | 40 mL | | |

The synthesis of an exemplary fluorous derivatized phosphoramidite 4e was achieved generally as follows and as outlined in FIG. 4 below. $Rf_6$ propanol (945 mg, 2.50 mmol, 1.0 equiv.) (FTI catalog #F017029) and Hunig's base (1.25 mL, 8.98 mmol, 3.60 equiv) were dissolved in 40 mL of $CH_2Cl_2$ in a 100 mL round bottom flask. 2-cyanoethyl diisopropylchlorophosphoramidite (Aldrich catalog #30, 230-9) (670 μL, 3.0 mmol, 1.20 equiv) was then added over 5 minutes and stirring continued at room temperature. After 1 h the reaction was complete as observed by the disappearance of propanol by TLC (Eluent: 20% ethyl acetate in hexanes; Visualization: $KMnO_4$ stain; $Rf_6$ propanol: $R_f$=0.30; Product phosphoramidite: $R_f$=0.70). The reaction was diluted with $CH_2Cl_2$ (60 mL) and the organic layer was quickly washed with $H_2O$, sat. $NaHCO_3$ solution, and sat. $NH_4Cl$ solution (25 mL each). The $CH_2Cl_2$ layer was concentrated by rotary evaporation and the residue subjected to a silica gel filtration in a 60 mL fritted glass funnel using 20% ethyl acetate in hexanes (~150 mL). The filtrate was concentrated by rotary evaporation and dried in vacuo to provide a clear, colorless oil. Molecular Weight: 578.36 for Molecular Formula: $C_{18}H_{24}F_{13}N_2O_2P$. Yield: 1.20 g, 81% yield. Purity: >95% by GC. $^1H$ NMR ($CDCl_3$)δ: 3.57-3.87 (m, 6H), 2.65 (t, 2H), 2.10-2.38 (m, 2H), 1.89-2.01 (m, 2H), 1.17-1.21 (2 overlapping doublets, 12H).

Example 2

Preparation of Capping reagent 2: 2-cyanoethyl-N'N'-diisopropyl-3-perfluorooctyl-propyloxy phosphoramidite

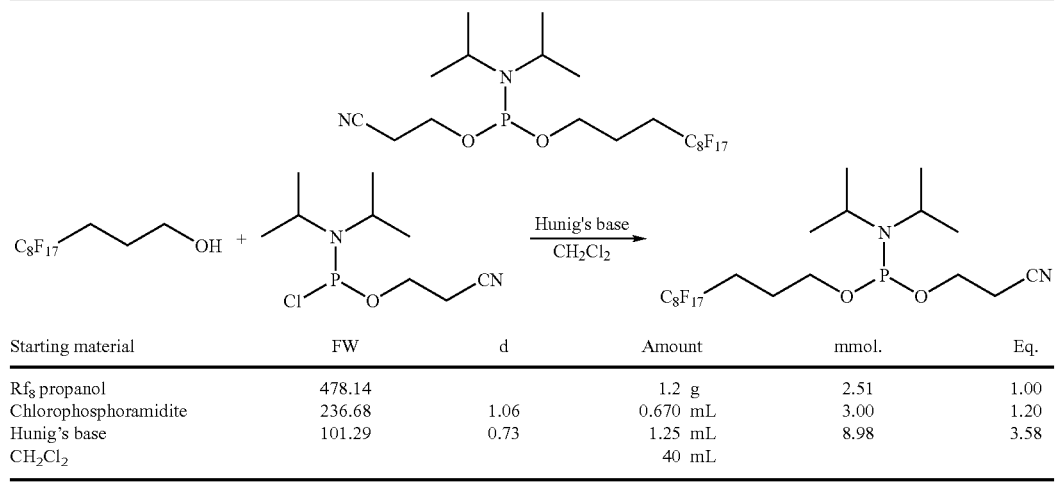

| Starting material | FW | d | Amount | mmol. | Eq. |
|---|---|---|---|---|---|
| $Rf_8$ propanol | 478.14 | | 1.2 g | 2.51 | 1.00 |
| Chlorophosphoramidite | 236.68 | 1.06 | 0.670 mL | 3.00 | 1.20 |
| Hunig's base | 101.29 | 0.73 | 1.25 mL | 8.98 | 3.58 |
| $CH_2Cl_2$ | | | 40 mL | | |

Rf₈ propanol (1.20 g, 2.51 mmol, 1.0 equiv.) and Hunig's base (1.25 mL, 8.98 mmol, 3.58 equiv) were dissolved in 40 mL of $CH_2Cl_2$ in a 100 mL round bottom flask. The chlorophosphoramidite (670 μL, 3.0 mmol, 1.20 equiv) was then added over 5 minutes and stirring continued at room temperature. After 1 h the reaction was complete as observed by the disappearance of propanol by TLC (Eluent: 20% ethyl acetate in hexanes; Visualization: $KMnO_4$ stain Rf₈ propanol: $R_f$=0.30; Product phosphoramidite: $R_f$=0.70). The reaction was diluted with $CH_2Cl_2$ (60 mL) and the organic layer was quickly washed with $H_2O$, sat. $NaHCO_3$ solution, and sat. $NH_4Cl$ solution (25 mL each). The $CH_2Cl_2$ layer was concentrated by rotary evaporation and the residue subjected to a silica gel filtration in a 60 mL fritted glass funnel using 20% ethyl acetate in hexanes (~150 mL). The filtrate was concentrated by rotary evaporation and dried in vacuo to provide an orange oil. Molecular Weight: 678.36 for Molecular Formula: $C_{20}H_{24}F_{17}N_2O_2P$. Yield: 1.40 g, 82% yield. Purity: >88% by GC. $^1H$ NMR ($CDCl_3$) δ: 3.57-3.87 (m, 6H), 2.65 (t, 2H), 2.10-2.38 (m, 2H), 1.89-2.01 (m, 2H), 1.17-1.21 (2 overlapping doublets, 12H).

Example 3 i. Automated, Cycled Solid-Phase Oligonucleotide Synthesis Procedures Using a Fluorous Capping Reagent ($PFC_8C_3$ Phosphoramidite)

A poly-T (T-15) sequence was synthesized on the ABI 394 instrument using the trityl-off cycle and a modified capping protocol. This experiment was designed in such a way that the coupling efficiency for each nucleotide addition step was reduced. This was accomplished by reducing the phosphoramidite concentration from the standard 0.1 M to 0.02 M. The reduced efficiency ensured the production of sufficient concentrations of the truncated sequences to make this example clearly illustrate the utility of this invention to rapidly purify the desired oligonucleotide away from the failure sequences. Standard base phosphoramidites were added using the standard 1 umol synthesis cycle with 30 s coupling time. $PFC_8C_3$ phosphoramidite was dissolved in acetonitrile at a concentration of 0.1 M and placed at bottle position 5 on the DNA synthesizer. The standard capping cycle was replaced by the $PFC_8C_3$ phosphoramidite+activator coupling cycle with a 200 sec coupling time. The oligonucleotide was subjected to standard deprotection conditions (30% ammonium hydroxide at 55° C. overnight) and stored at −20° C. until needed for cartridge purification. An aliquot was desalted into 1×TE with a NAP-10 column, and analyzed by ion-exchange HPLC using a gradient of sodium chloride in 20 mM sodium hydroxide on a Dionex Nucleopak-100 column.

ii. Oligodeoxyribonucleotide Deprotection

The solid support was removed from the column and exposed to 1 ml concentrated ammonium hydroxide at room temperature for four hours in a closed tube. The support was then removed by filtration and the solution containing the partially protected oligodeoxynucleotide was brought to 55° C. for five hours. Ammonia may be removed, however, an advantage of the present invention is that the residue can be directly purified as described below without removal of ammonia.

Example 4

Removal of Capped Failure Sequences from Unprotected Oligonucleotide by Fluorous Cartridge Purification The utility of the fluorous method for oligonucleotide purification was illustrated using solid-phase extraction ("SPE" or "cartridge purification"). The crude deprotected oligonucleotide (4a and 5b) was diluted with an equal volume of loading buffer (10% sodium chloride and 5% dimethylformamide in water) purchased from Berry and Associates, Dexter, Mich. A fluorous affinity cartridge (fluoro-pak II) was also purchased from Berry and Associates, Dexter, Mich., and preconditioned by passing 2 mL acetonitrile followed by 2 mL 0.1 M triethylammonium acetate (TEAA), further followed by 2 mL of loading buffer. A flow rate of 2 seconds per drop was maintained in these steps as recommended by the manufacturer. The purification of the crude oligonucleotide was accomplished by simply passing the oligonucleotide and loading buffer mixture through the preconditioned column at a flow rate of 5 seconds per drop, whereby the desired full-length oligonucleotide passed through the column and the contaminating fluorous capped failure sequences were quantitatively retained. An additional quick NAP-10 desalting step was sufficient to remove ammonia and salt from the oligonucleotide. The failure sequences were eluted from the fluorous cartridge and analyzed by anion exchange HPLC.

HPLC analysis of these crude oligonucleotide mixtures showed that the fluorous-capped full-length oligonucleotides are highly retained on a fluorous HPLC adsorbent. To illustrate the magnitude of retention, FIG. 5 shows an HPLC analysis of crude fluorous-capped T-15 showing the presence of failure and correct sequences. FIG. 6 shows an HPLC analysis of the product filtered through a FLURO-PAK™ fluorous cartridge. The eluate showed complete binding of the capped oligomers (failure sequences), while most of the non-fluorous material (the correct sequence) failed to bind. DMT-on purifications cannot achieve this level of selectivity on long oligonucleotides. FIG. 7 shows an HPLC analysis of the impurities released from the column after filtration through a fluorous cartridge by washing the column with 40% acetonitrile in 0.1 M TEAA. The eluant shows the removal of the failure sequences. These figures show that the fluorous-capped material 4a is strongly retained over the non-fluorous capped 15-mers, eluting only when the acetonitrile percentage neared 50% in the gradient profile. Note that an isocratic elution gave even larger differences in retention times. FIG. 8 shows the HPLC analysis of the filtrate containing the fluorous-purified 15-mer oligonucleotide after a NAP-10 desalting step. These examples show that the present method allows for an easy separation of the full-length oligonucleotide away from failure sequences. Because of the efficiency of the purification the full length oligonucleotide may be obtained in high yield and purity.

All publications, patents, accession number, and patent applications cited in this specification are herein incorporated by reference as if each individual publication or patent application were specifically and individually indicated to be incorporated by reference for all purposes.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the invention as defined herein and in the appended claims. For example, all the techniques and apparatus described above may be used in various combinations.

What is claimed is:

1. A compound having the formula (I):

$$PR^1R^2R^3 \quad (I)$$

wherein $R^1$ is selected from the group consisting of $C_1$-$C_8$alkyloxy, $C_1$-$C_8$alkenyloxy and $C_1$-$C_8$alkynyloxy, optionally substituted with CN;

$R^2$ is halogen or $NR^4_2$;

$R^3$ has the formula -L-A;

each $R^4$ is $C_1$-$C_6$alkyl or are combined to form a 4 to 7 membered heterocyclic ring, optionally substituted with from 1 to 3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl;

L is —$C_1$-$C_{10}$alkyleneoxy-, which is optionally substituted with from 1-3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl-; and A is $C_1$-$C_{30}$perfluoroalkyl.

2. The compound of claim 1, wherein $R^1$ is —$OCH_3$.

3. The compound of claim 1, wherein $R^1$ is —O—$CH_2CH$=$CH_2$.

4. The compound of claim 1, wherein $R^1$ is —$OCH_2CH_2CN$.

5. The compound of claim 1, wherein $R^2$ is halogen.

6. The compound of claim 1, wherein $R^2$ is selected from the group consisting of —$N(Me)_2$, —$N(Et)_2$, —$N(Pr)_2$, —$N(i\text{-}Pr)_2$, 1-pyrrolidnyl, 1-piperidinyl, 4-morpholinyl and 1-imidazolyl.

7. The compound of claim 1, wherein $R^2$ is —$N(i\text{-}Pr)_2$.

8. The compound of claim 1, wherein $R^3$ has the formula —O—$(CH_2)_m(CF_2)_pCF_3$; m is 1, 2, 3, 4, 5, 6, 7, 8, 9 or 10 and p is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

9. A compound of claim 1, wherein m is 3 and p is 5.

10. A compound of claim 1, wherein m is 3 and p is 7.

11. A method of inhibiting extension of an oligonucleotide, the method comprising contacting an oligonucleotide with a compound of claim 1 with or without a catalyst.

12. A method of preparing a modified oligonucleotide comprising X nucleotides wherein X is an integer of at least 3; the method comprising (a) contacting a plurality of oligonucleotides, each comprising X-n nucleotide units, with a modified nucleotide or nucleoside, wherein n is an integer from 1 to X−1; and (b) contacting unreacted product of (a) with a capping reagent comprising a perfluoroalkyl affinity handle.

13. A method of preparing a modified oligonucleotide comprising X nucleotides wherein X is an integer of at least 3; the method comprising (a) contacting a plurality of oligonucleotides, each comprising X-n nucleotide units, with a modified nucleotide or nucleoside, wherein n is an integer from 1 to X−1; and (b) contacting unreacted product of (a) with a capping reagent comprising a compound of claim 1.

14. An oligonucleotide comprising at least one modified nucleoside moiety comprising the formula:

$$Nu\text{~}OP(OR^3)(NR^4_2);$$

wherein Nu is a nucleoside;

$R^3$ has the formula -LA;

each $R^4$ is $C_1$-$C_6$alkyl or are combined to form a 4 to 7 membered heterocyclic ring, optionally substituted with from 1 to 3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl;

L is $C_1$-$C_{10}$ alkyleneoxy, which is optionally substituted with from 1-3 substituents selected from the group consisting of $C_1$-$C_6$alkyl-, $C_1$-$C_6$haloalkyl-, $C_1$-$C_6$alkoxy-, aryl$C_1$-$C_6$alkoxy-, oxo- and $C_1$-$C_6$alkoxycarbonyl-;

A is $C_1$-$C_{30}$perfluoroalkyl; and

~indicates the point of attachment to a hydroxyl oxygen of the nucleoside.

15. A composition comprising at least one compound of claim 1.

16. A kit for preparing a nucleic acid, comprising at least one compound of claim 1.

17. A kit of claim 16 for preparing a nucleic acid, further comprising at least one of (a) at least one extendible monomer; (b) at least one solid support; (c) at least one catalyst for use in extending the oligonucleotide; (d) at least one buffer; (e) at least one set of instructions for extending the oligonucleotide using with the components of the kit; and (f) at least one a container for packing the components of the kit.

* * * * *